United States Patent [19]

Murphy et al.

[11] Patent Number: 5,215,985

[45] Date of Patent: Jun. 1, 1993

[54] METHOD FOR TREATING ISCHEMIC INSULT TO NEURONS EMPLOYING AN ATP-SENSITIVE POTASSIUM CHANNEL BLOCKER

[75] Inventors: Kerry P. S. J. Murphy, South Croydon Surrey; Susan A. Greenfield, Oxford, both of United Kingdom

[73] Assignee: E. R. Squibb & Sons, Inc., Princeton, N.J.

[21] Appl. No.: 826,546

[22] Filed: Jan. 27, 1992

Related U.S. Application Data

[63] Continuation of Ser. No. 556,502, Jul. 20, 1990, abandoned.

[51] Int. Cl.$^5$ .................. A61K 31/55; A61K 31/495; A61K 31/175

[52] U.S. Cl. .................... 514/212; 514/255; 514/592; 514/593

[58] Field of Search ............... 514/212, 255, 592, 593

[56] References Cited

U.S. PATENT DOCUMENTS 3,825,665  7/1974  Weber et al. .................. 514/593
3,932,658  1/1976  Weber et al. .................. 514/593

OTHER PUBLICATIONS

Mourre, Res. C et al. Brain Research 486:159-64 (1989).

Primary Examiner—Allen J. Robinson
Assistant Examiner—Gary E. Hollinden
Attorney, Agent, or Firm—Burton Rodney

[57] ABSTRACT

A method is provided for treatment of neuronal insult, such as caused by lack of oxygen, by administering an ATP-sensitive potassium channel blocker, such as a sulfonyl urea, for example, tolbutamide.

6 Claims, 4 Drawing Sheets

METHOD FOR TREATING ISCHEMIC INSULT TO NEURONS EMPLOYING AN ATP-SENSITIVE POTASSIUM CHANNEL BLOCKER

This is a continuation of application Ser. No. 556,52, filed Jul. 20, 1990 abandoned.

FIELD OF THE INVENTION

The present invention relates to a method for treating neuronal insult, such as caused by lack of oxygen, in neurons prone to Parkinsonian degeneration, by administering to a patient an ATP-sensitive potassium channel blocker.

BACKGROUND OF THE INVENTION

A species of potassium channel that is dependent on adenosine triphosphate (ATP) was first described in cardiac muscle by Noma A. (1983), "ATP-regulated $K^+$ channels in cardiac muscle," Nature 305: 147-148. This channel has attracted increasing interest due to its unusual and close association with cell metabolism. Ashcroft, F. M. (1988), "Adenosine 5-triphosphate-sensitive potassium channels," Ann. Rev. Neurosci. 11: 97-118. It is now well established that ATP-sensitive potassium channels are present in diverse tissues i.e. cardiac muscle, (Kakei M. and Noma A. (1984) "Adenosine 5′-triphosphate-sensitive single potassium channel in the atrioventricular node cell of the rabbit heart," J. Physiol. 352: 265-284, Noma A. and Shibasake, T. (1985), "Membrane current through adenosine-triphosphate-regulated potassium channels in guinea-pig ventricular cells," J. Physiol. 363: 463-480), pancreatic beta cells (Findlay, I., Dunne, M. J., and Petersen, O. H. (1985a), "ATP-sensitive inward rectifier and voltage- and calcium activated $K^+$ channels in cultured pancreatic islet cells," J. Memb. Biol. 88: 165-172; Dunne, M. J., Findlay, I., Petersen, O. H. and Wollheim, C. B. (1986), "ATP-sensitive $K^+$ channels in an insulin-secreting cell line are inhibited by D-glyceraldehyde and activated by membrane permeabilization." J. Memb. Biol. 93: 271-279; Ashcroft, F. M. et al (1984), "Glucose induces closure of single potassium channels in isolated rat pancreatic $\beta$-cells," Nature 312: 446-448); skeletal muscle (Sturgess, N. C., Ashford, M. L. J., Cook, D. L. and Hales, C. N. (1985), "The sulphonylurea receptor may be an ATP-sensitive potassium channel," Lancet 8435: 474-475) and smooth muscle (Standen, N. B., Quayle, J. M., Davies, N. W., Brayden, J. E., Huang, Y. and Nelson, M. T. (1989), "Hyperpolarizing vasodilators activate ATP-sensitive $K^+$ channels in arterial muscle," Science 245: 177-180). More recently, indirect evidence has suggested that the ATP-sensitive channel may also be present in the brain: sulfonylureas, which are potent blocking agents of this channel in heart and beta cells, display selective binding in certain brain regions (Mourre, C., Ben Ari, Y., Bernardi, H., Fosset, M. and Lazdunski, M. (1989), "Antidiabetic sulfonylureas: localization of binding sites in the brain and effects on the hyperpolarization induced by anoxia in hippocampal slices," Brain Res. 486: 159-164) and indeed an endogenous ligand for a central sulfonylurea receptor has been described (Virsolvy-Vergine, A., Bruck, M., Dufour, M., Cauvin, A., Lupo, B. and Bataille, D. (1988), "An endogenous ligand for the central sulfonylurea receptor," FEBS Letters 242: 65-69). It has also been found that sulfonylurea binding sites appear to be highest in regions of the brain associated with the control of movement, i.e. motor cortex, cerebellar cortex, globus pallidus and substantia nigra (Mourre et al., supra, 1989).

Despite intensive research into the causes and cures for Parkinson's disease, the actual homeostatic mechanisms of physiological and indeed pathological neuronal regulation within the substantia nigra remain obscure In the brain, the substantia nigra has the highest density of binding sites for the sulphonylurea, glibenclamide (Mourre, C. et al, Brain Res. 486, 159-164 (1989)), a selective blocker of $K_{ATP}$ (Sturgess, N., et al, Lancet ii 8453, 474-475 (1985); Schmid-Antomarchi, H., et al Biochem. Biophys. Res. Commun. 146, 21-25 (1987); and Weille de, J., et al, Proc. Natl. Acad. Sci. U.S.A. 85, 1312-1316 (1988)). It is thus possible that in the substantia nigra this channel, which has an unusual and close association with cell metabolism (Ashcroft, F. M., Rev. Neurosci. 11, 97-118 (1988)), may play a pivotal role in neuronal regulation.

DESCRIPTION OF THE INVENTION

It has now been found that the $K_{ATP}$ channel is critical in the responses of nigral neurons to changes in the neuronal microenvironment, for example, during ischaemia. It has further been found that ischaemia causes the opening of potassium channels in a selective population of neurons with distinct pharmacological and electrophysiological properties. Under ischaemic conditions, these neurons are prone to Parkinsonian degeneration.

Thus, in accordance with the present invention, a method is provided for treating neuronal insult, in the brain, due to lack of oxygen, wherein a therapeutically effective amount of a pharmaceutical which blocks an ATP-sensitive potassium channel in the brain is administered to a mammalian species in need of such treatment.

In addition, in accordance with the present invention, a method is provided for treating early stages of Parkinsonian degeneration-compensation, as caused by ischemic insult to neurons prone to Parkinsonian degeneration, wherein a therapeutically effective amount of a pharmaceutical which blocks an ATP-sensitive potassium channel in the brain is administered to a mammalian species in need of such treatment.

The ischaemic insult referred to above may result from lack of oxygen to neurons prone to Parkinsonian degeneration such as caused by exposure to toxic fumes, for example, as caused by pyridines or cyanide poisoning, which results in reduced oxygen consumption in the cell.

The pharmaceutical employed in the methods of the present invention will be an effective blocker of the ATP-sensitive potassium channel in the brain. Examples of such a pharmaceutical include, but are not limited to sulfonyl ureas such as glyburide (1-[[p-[2-(5-chloro-O-anisamido)-ethyl]phenyl]sulfonyl]-3-cyclohexylurea); chloropropamide(1-[(p-chlorophenyl)sulfonyl]-3-propylurea); glibenclamide; glipizide(1-cyclohexyl-3-[[p-[2-(5-methyl-pyrazinecarboximido)ethyl]phenyl]sulfonyl]-urea); tolazamide(benzenesulfonamide-N-[[(hexahydro-1H-azepin-1-yl)amino]-carbonyl,-4-methyl), or tolbutamide (benzenesulfoamide,N-(butylamino)carbonyl]-4-methyl), with the latter being preferred. In addition, quinine may also be employed in place of the sulfonyl urea.

Although the K-ATP channel blocker employed in the methods of the invention may be administered systemically, such as orally or parenterally, it is preferred that the K-ATP channel blocker be administered locally, for example, by carotid injection, lumbar puncture or cisternal puncture. The K-ATP blocker will be administered for as long as a treatment for neuronal insult due to lack of oxygen or treatment for early stages of Parkinsonian degeneration-compensation is required.

With regard to dosage of K-ATP channel blocker, where a wide region of the brain is to be treated, for example, by intracarotid injection, lumbar puncture or cisternal puncture, from about 0.1 to about 20 mg/kg/treatment and preferably from about 0.5 to about 15 mg/kg/treatment will be employed, depending upon the particular K-ATP channel blocker employed.

Where the K-ATP channel blocker is to be administered sytemically, such as orally or parenterally, it will be administered in an amount to achieve a steady state level of K-ATP channel blocker in the blood. Thus, for systemic treatment, the K-ATP channel blocker may be administered in an amount within the range of from about 0.5 to about 20 mg/kg for each treatment and preferably from about 1 to about 15 mg/kg for each treatment.

In carrying out the method of the present invention, the K-ATP channel blocker may be administered to mammalian species, such as monkeys, dogs, cats, rats, and humans. The K-ATP channel blocker may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like.

Figure 1A:
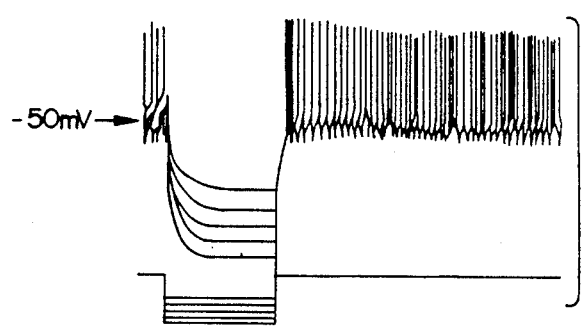
FIGS. 1 to 3 are graphs or chart recordings which depict data obtained in carrying out the experiment described in Example 5.

The following Examples represent preferred embodiments of the present invention.

EXAMPLE 1

An injectable solution for use in administering tolbutamide by injection in the carotid artery or by lumbar puncture or cisternal puncture for treating neuronal insult or early stages of Parkinsonian degeneration-compensation is produced as follows:

| Tolbutamide | 250 mg |
|---|---|
| Sodium chloride | 25 mg |
| Polyethylene glycol 400 | 1.5 l |
| Water for injection qs. | 5 l. |

The tolbutamide and sodium chloride are dissolved in 1.5 liters of polyethylene glycol 400 and 3 liters of water for injection and then the volume is brought up to 6.5 liters. The solution is filtered through a sterile filter and aseptically filled into presterilized vials which are then closed with presterilized rubber closures. Each vial contains 25 ml of solution in a concentration of 50 mg of active ingredient per ml of solution for injection.

EXAMPLE 2

An injectable for use in treating neuronal insult or early stages of Parkinsonian degeneration-compensation is prepared as described in Example 1 except that quinine is employed in place of tolbutamide.

EXAMPLE 3 AND 4

An injectable for use in treating neuronal insult or early stages of Parkinsonian degeneration-compensation is prepared as described in Example 1 except that glyburide or glipizide is employed in place of tolbutamide.

EXAMPLE 5

Recent evidence suggests that an APT-sensitive potassium channel is present in the brain. From ligand binding studies it has been inferred that this relatively unfamiliar channel is particulary densely distributed in areas associated with motor control. To ascertain the role of the ATP-K channel in the in vitro substantia nigra a model of ischaemia was used to lower intracellular ATP and the sulphonylurea tolbutamide was used to assess the activation of ATP-K channels.

METHODS

Coronal slices of adult male guinea-pig mesencephalon were prepared as described by Harris, Webb et al, Neurosci. 31, 363-730 (1989) with the exception that halothane was used as the anaesthetic. Slices were perfused in the recording chamber with the following solution (in mM): NaCl 136, KCl 2, $NaHCO_3$ 26, $KH_2PO_4$ 1.25, $MgSO_4$ 2, $CaCl_2$ 2.4, glucose 10.7. Intracellular recordings were made in pars compacta neurons at the level of the mammillary bodies (Gustafson, E.L. et al, Brain Res. 491, 297-306 (1989)), with microelectrodes filled with 3M potassium acetate (series resistance measured in csf 50-140 Mohm). Neurons were characterised by an ability to generate burst firing triggered from a slow inward current ('$LTSgCa^{2+}$'), activated by either a depolarizing or hyperpolarizing current pulse from a hyperpolarized membrane potential (Llinas et al, Brain Res., 294, 127-132 (1984), and Kita et al, Brain Res. 372, 21-30 (1986)). All drugs were applied via the perfusing solution to effective concentrations stated. Tolbutamide was initially prepared as a 0.5M stock solution dissolved in DMSO.

FIG. 1

Action of cyanide and tolbutamide on membrane potential, input resistance, firing frequency and generation of $LTSgCa^{2+}$ evoked burst firing. Cell characteristics:apparent membrane potential, −50 mV; input resistance 113 Mohms; firing frequency, 28 Hz; exhibited $LTSgCa^{2+}$. a: membrane response to injections of hyperpolarizing current. b: generation of $LTSgCa^{2+}$ evoked burst firing, activated by depolarizing phase of a 0.6 nA hyperpolarizing pulse from a hyperpolarized membrane potential. c: control response prior to exposure to cyanide. d: in 100 $\mu M$ cyanide. e: in 200 $\mu M$ cyanide, note change in input resistance, hyperpolarization and generation of $LTSgCa^{2+}$. f: in 200 $\mu M$ cyanide and 50 $\mu M$ tolbutamide. Hyperpolarizing pulse in C to F was 0.4 nA for 200 ms.

FIG. 2

Chart record illustrating the time course of a typical experiment showing the actions of cyanide on the electrophysiological properties of a pars compacta neuron (same as in FIG. 1). Hyperpolarizing pulses (0.4 nA, 200 ms) were given at 0.2 Hz. Bath applied cyanide (1-200 $\mu M$) induced dose-dependent decreases in firing frequency and input resistance together with membrane hyperpolarization. The actions of 200 $\mu M$ cyanide were abolished by the presence of 50 μM tolbutamide in the bathing medium. Action potentials attenuated by frequency response of chart recorder.

FIG. 3

Current-voltage relations of a nigrostriatal cell obtained prior to and during exposure to cyanide. Cell characteristics: apparent membrane potential, −55 mV; input resistance, 113 Mohms; firing frequency, 2 Hz, exhibited LTSgCa$^{2+}$ a membrane response to hyperpolarizing current pulses, note time-dependent anomalous rectification. b: membrane response to hyperpolarizing current pulses in the presence of 400 μM cyanide. c: plot of current-voltage relations prior to (open circles) and during exposure to 400 μM cyanide. Each data point is average of measurements made from 4 successive pulses, standard deviations lost within the symbol. Measurements made at 57 ms and 180 ms to allow for anomalous rectification. Lines fitted to data are simple regression lines with correlation coefficients ($r^2$) >0.997. The bathing medium contained 3.2 mM KCl at 33° C, assuming K$^+_i$=140 mM). The current-voltage plots interesect at −92 mV, this together with the decrease in input resistance seen in the presence of cyanide suggests that cyanide increases membrane permeability to potassium ions.

Figure 1B:
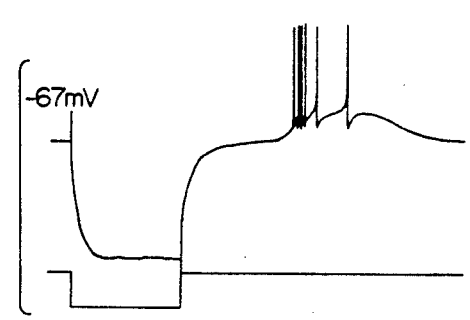
Figure 1C:
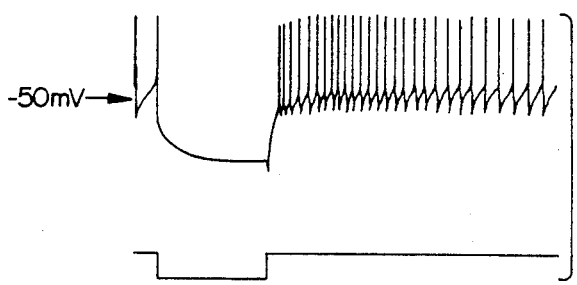
Figure 1D:
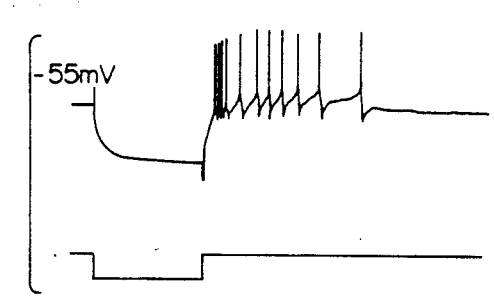
Figure 1E:
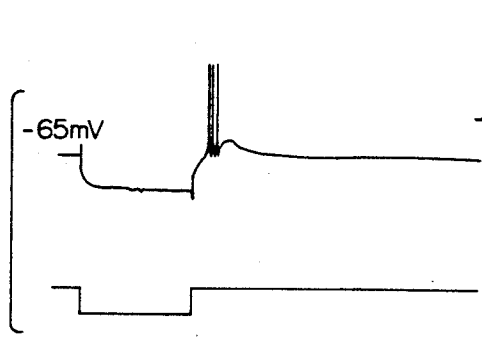

Long-term recordings (30 min–4 hr) were made from a total of 30 cells located in the pars compacta region of the substantia nigra. Of these 18 resembled nigral neurons described previously, 5. (Llinas, R., et al, supra; Kita, T., et al, supra; Nedergaard, S., et al, Exp. Brain Res. 69, 444–448 (1988); Greenfield, S.A., et al, Exp. Brain Res. 70, 441–444 (1988); Kapoor, R., et al, Exp. Brain Res. 74, 653–657 (1989); Harris, N. C., et al, Exp. Brain Res. 74, 411–416 (1989)), in that a slow inward current ('LTSgCa$^{2+}$') (Llinas, R., et al, supra), could be triggered in these neurons upon depolarization from a hyperpolarized resting potential: this LTSgCa$^{2+}$ in turn led to the generation of bursts of action potentials (FIG. 1b). Furthermore, this population of neurons was sensitive to application of the dopamine (DA) receptor competitive antagonist, haloperidol (10–100 μM), which caused a decrease in resting potential and/or an increase in firing rate (depolarization 11+/−4 mV standard deviation (SD), 13 fold increase in firing rate, n=4).

Figure 1F:
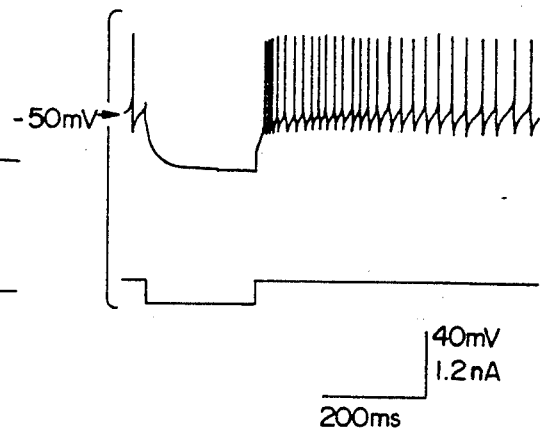
Figure 2:
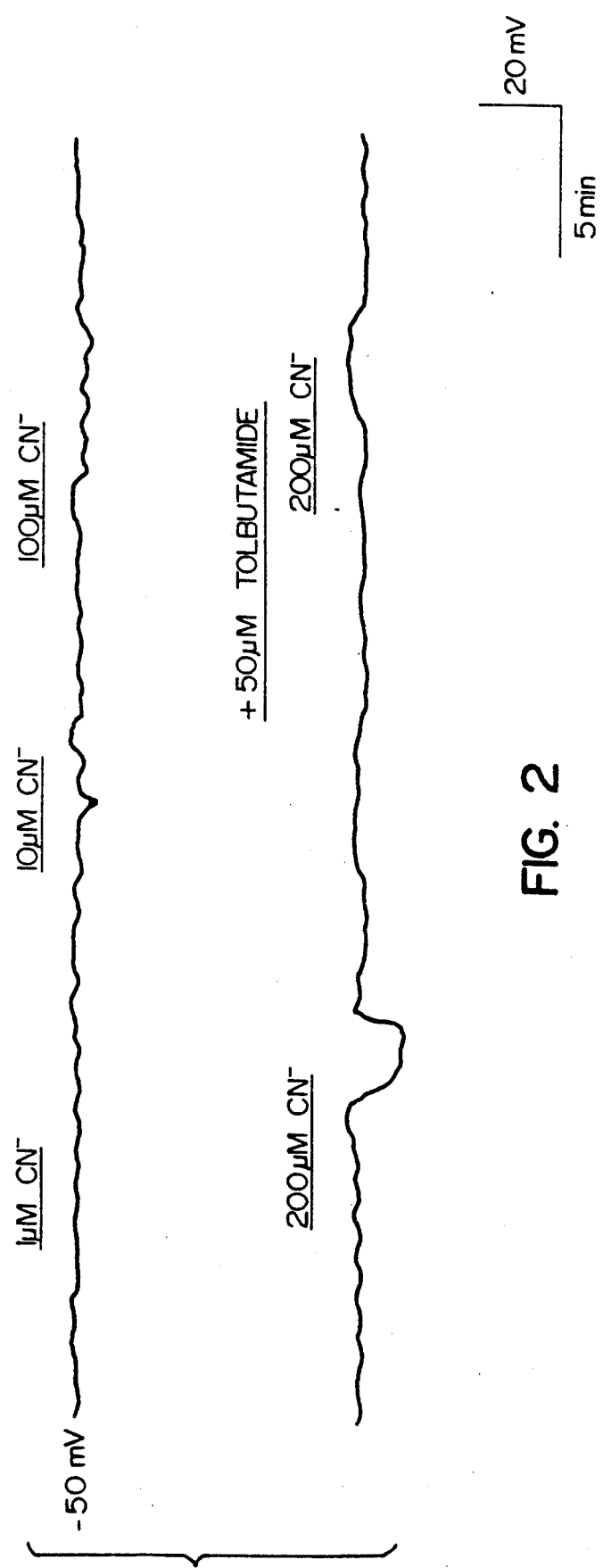
Figure 3A:
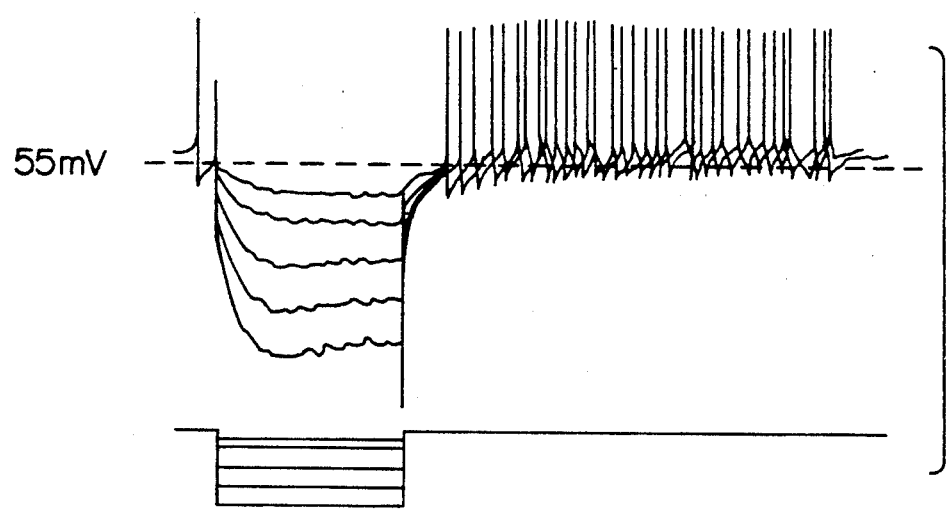
Figure 3B:
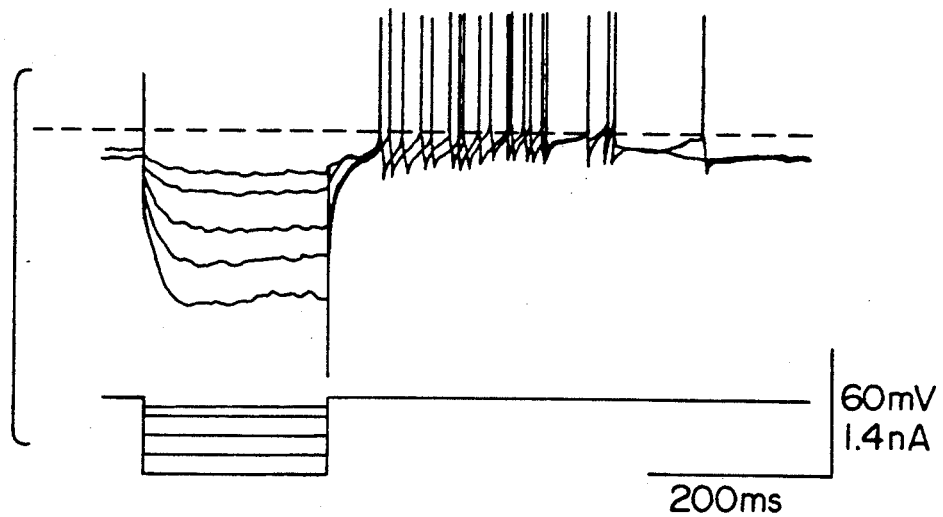
Figure 3C:
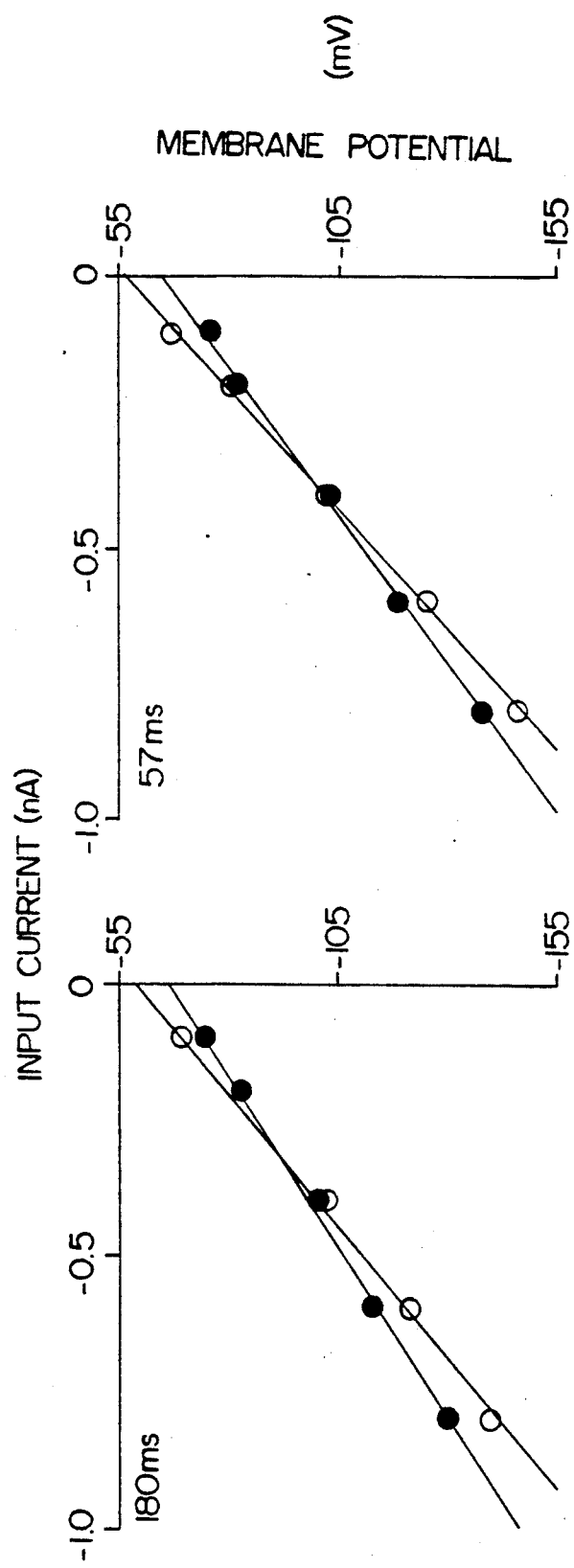

When these neurons (n=15) were exposed to cyanide (1–400 μM), a marked response was seen (FIG. 2), consisting of a hyperpolarization (10+/−4 mV SD, n=15) accompanied by a decrease in input resistance (prior to cyanide 112+/−9.6 Mohms standard error of the mean (SEM), n=13; during cyanide 84+/−7.7 Mohms SEM, n=13; P<0.001 paired Student's t-test) and a decrease in firing rate (prior cyanide 18+4.1 Hz SEM, n=12; during cyanide 1.4+0.8 Hz SEM, n=12; P<0.001 paired Student's t-test) which were reversed as soon as the cyanide was withdrawn (FIG. 2). The action of cyanide on the current-voltage relationship for these neurons suggested that cyanide-induced hyperpolarization was attributable to the opening of potassium channels (FIG. 3, mean cyanide reversal potential, −96+/−4 mV SD, n=3). However, the effects of cyanide were completely abolished in the presence of the sulphonylurea tolbutamide (50–100 μM), a selective blocker of K$_{APT}$ channels (Trube, G., et al, Pfluegers Arch. 407, 493–499 (1986), Belles, B., et al, Pfluegers Arch. 409, 582–588 (1987)), (n=6) (FIG. 1f and 2). Indeed, in the presence of tolbutamide, cyanide poisoning led to a small depolarization of the resting potential (FIG. 2). By contrast a second population of nigral neurons recorded in this study (n=12) did not display a LTSgCa$^{2+}$, burst firing, nor sensitivity to haloperidol (n=5). Furthermore, exposure to cyanide did not result in a hyperpolarization of the resting potential of these cells (n=6).

The observation that cyanide-induced hyperpolarization only occurred in a certain population of nigral cells precludes a non-specific action at the level of the membrane. Rather, the small depolarizations observed in the presence of tolbutamide, or in the haloperidol-insensitive cells during cyanide application, is most simply attributable to a gradual impairment of the ubiquitous sodium-potassium pump. The cells that were normally hyperpolarized by cyanide were characterized by generation of the LTSgCa$^{2+}$, has been shown to be indicative of long 'apical' dendrites extending into the pars reticulata region of the substantia nigra (Harris et al, supra). It is these long dendrites which are known to probably release DA (Glowindki, J., et al Chemical Neurotransmission (eds Stjarne, et al; Academic Press London) 245–299 (1981)). In addition, the excitation of these cells by haloperidol strongly suggests that they are under the tonic influence of endogenous dendritic DA (see Nedergaard et al, supra, and Kapoor et al, supra). This finding thus prompts the hypothesis that it is those nigral neurons controlled by dendritic DA which possess the means for a rapid response (ie the K$_{ATP}$ channel) to changes in the extracellular melieu. The observations described here show that ischaemia in these neurons is sensitively and selectively reflected in an opening of tolbutamide-sensitive potassium channels. Indeed, the cyanide induced enhancement of the LTSgCa$^{2+}$ seen in FIG. 1e, despite a fall in input resistance would suggest a dendritic location for these channels on the apical dendrites, within the pars reticulata (Mourre et al, supra).

It should be noted that hyperpolarization deinactivates the LTSgCa$^{2+}$ which in turn leads to burst firing (Llinas et al, supra) and a non-linear increase in striated DA release (Gonon, G. G., Neurosci 10, 333–348 (1988)). Hence in the cases of mild anoxia, the K$_{ATP}$ could initiate a chain of events leading to functional neuronal compensation. This means of compensation for neuronal insult may be extended to the pre-symptomatic stages of Parkinsonism. Reduced oxygen consumption has been implicated in nigral cell death (Sanchez-Ramos, J. R., et al, Progress in Parkinson's Research (eds Hefti, F. & Wiener, W. J.; Plenum Press) 145–152 (1988)), and indeed the resultant K$_{ATP}$ mediated hyperpolarization would mimic operationally the normal action of local endogenous DA (Nedergaard et al, supra). Hence via the sequence of events outlined above, levels of striatal DA release would remain the same despite the reduced dendritic DA release in the pre-symptomatic yet pathological substantia nigra. It is possible therefore that the tolbutamide-sensitive potassium channel plays a vital role in both physiological regulation and pathological compensation in nigral cells controlled by local DA and hence analoguous to those prone to Parkinsonian degeneration. However as the degeneration process progressed, the resultant hyperpolarization via K-ATP channels would be so severe that firstly, the cell body as well as the dendrites would be hyperpolarized, and hence activation of the LTSgCa$^{2+}$ prevented (see Llinas et al, 1984, supra); secondly, the very high levels of extracellular K$^+$ ions would lead to

SUMMARY

Ischaemia causes the opening of potassium channels in a selective population of neurons with distinct pharmacological and electrophysiological properties. The response to ischaemia is abolished by tolbutamide. These results suggest that an ATP-K channel sensitive to ischaemia is present in the substantia nigra and furthemore it may play a pivitol role in normal and pathological mechanisms of homoeostasis. In addition, tolubutamide may be useful in treating insult to neurons prone to Parkinsonian degeneration.

What is claimed is:

1. A method for treating neuronal insult in the substantia nigra of the brain due to lack of oxygen, which comprises administering to the substantia nigra of the brain of a mammalian species in need of treatment, a therapeutically effective amount of a pharmaceutical which blocks an ATP-sensitive potassium channel in the substantia nigra of the brain and is effective in treating neuronal insult in the brain due to lack of oxygen, where the pharmaceutical is a sulfonyl urea which is tolbutamide, glyburide (1[p-2[5-chloro-O-anisamido)ethyl]phenyl]sulfonyl]-3-cyclohexyl-3-urea); chlopropamide (1-[[(p-chlorophenyl)sulfonyl]-3-propylurea; glipizide(1-cyclohexyl-3[[p-[2(5-methylpyrazinecarboxamido)ethyl]phenyl]sulfonyl]urea); or tolazamide(benzenesulfonamide-N-[[(hexahydro-1H-azepin-1yl-)amino]carbonyl]-4-methyl).

2. The method as defined in claim 1 wherein the sulfonyl urea is tolbutamide.

3. The method as defined in claim 1 wherein the pharmaceutical is administered by infusion into the substantia nigra and blocks the ATP-sensitive potassium channel.

4. The method as defined in claim 1 wherein the pharmaceutical is administered locally.

5. The method as defined in claim 1 wherein the pharmaceutical is administered locally by injection in the carotid artery, lumbar puncture or cisternal puncture.

6. The method as defined in claim 1 wherein the pharmaceutical is administered locally in an amount of from about 0.1 to about 20 mg/kg/treatment.

* * * * *

UNITED STATES PATENT AND TRADEMARK OFFICE
CERTIFICATE OF CORRECTION

PATENT NO.   : 5,215,985
DATED        : June 1, 1993
INVENTOR(S)  : Kerry P.S.J. Murphy et al It is certified that error appears in the above-indentified patent and that said Letters Patent is hereby corrected as shown below:

In the claims, Column 8, line 2, last word should read --chlorpropa--;

Column 8, line 6 should read --zenesulfonamide-N-[[(hexahydro-1H-azepin-1-yl- --.

Signed and Sealed this

Twenty-ninth Day of March, 1994

Attest:

BRUCE LEHMAN

Attesting Officer      Commissioner of Patents and Trademarks